(12) United States Patent
Grose (10) Patent No.: US 12,306,168 B2
(45) Date of Patent: May 20, 2025

(54) HYDROCARBON CONDENSATE DETECTION AND CONTROL

(71) Applicant: Dean Grose, Eighty Four, PA (US)

(72) Inventor: Dean Grose, Eighty Four, PA (US)

( * ) Notice: Subject to any disclaimer, the term of this patent is extended or adjusted under 35 U.S.C. 154(b) by 581 days.

(21) Appl. No.: 17/410,560

(22) Filed: Aug. 24, 2021

(65) Prior Publication Data

US 2021/0382030 A1 Dec. 9, 2021

Related U.S. Application Data (63) Continuation-in-part of application No. 17/091,800, filed on Nov. 6, 2020, now Pat. No. 11,613,458, and a continuation-in-part of application No. 17/024,673, filed on Sep. 17, 2020, now Pat. No. 11,725,972, said application No. 17/091,800 is a continuation-in-part of application No. 17/024,673, filed on Sep. 17, 2020, now Pat. No. 11,725,972.

(60) Provisional application No. 63/034,945, filed on Jun. 4, 2020, provisional application No. 63/022,351, filed on May 8, 2020, provisional application No. 62/978,015, filed on Feb. 18, 2020.

(51) Int. Cl.
| | |
|---|---|
| *G01N 21/64* | (2006.01) |
| *B67D 7/32* | (2010.01) |
| *B67D 7/34* | (2010.01) |
| *G01N 21/25* | (2006.01) |
| *G01N 21/53* | (2006.01) |
| *G01N 21/85* | (2006.01) |
| *G01N 33/28* | (2006.01) |
| *G01N 21/84* | (2006.01) |

(52) U.S. Cl.
CPC ....... *G01N 33/2835* (2013.01); *B67D 7/3245* (2013.01); *B67D 7/342* (2013.01); *G01N 21/251* (2013.01); *G01N 21/534* (2013.01); *G01N 21/64* (2013.01); *G01N 21/8507* (2013.01); *G01N 2021/6491* (2013.01); *G01N 2021/8416* (2013.01); *G01N 2021/8557* (2013.01)

(58) Field of Classification Search
CPC .......... G01N 33/2835; G01N 33/1833; G01N 21/53; G01N 21/643; G01N 21/85; G01N 21/251; G01N 21/534; G01N 21/64; G01N 21/8507; G01N 2021/6491; G01N 2021/8416; G01N 2021/8557; B67D 7/342; B67D 7/3245
See application file for complete search history.

(56) References Cited

U.S. PATENT DOCUMENTS

| | | | | |
|---|---|---|---|---|
| 5,257,085 | A * | 10/1993 | Ulich ................. | G01J 3/2823 356/73 |
| 5,304,492 | A * | 4/1994 | Klinkhammer ...... | G01N 21/645 356/417 |
| 5,489,977 | A * | 2/1996 | Winslow .............. | G01N 21/645 356/73 |
| 8,084,756 | B2 * | 12/2011 | Tokhtuev ........... | G01N 21/6402 250/573 |

(Continued)

*Primary Examiner* — Nicolas A Arnett
(74) *Attorney, Agent, or Firm* — Richard W. James (57) ABSTRACT

Hydrocarbon condensate detection and control. The hydrocarbon condensate detection and control system includes detecting hydrocarbon in an aqueous mixture by sensing fluorescence, turbidity, and color of the aqueous mixture and controlling the flow of the aqueous mixture based on the hydrocarbon content of the aqueous mixture.

20 Claims, 6 Drawing Sheets

(56) References Cited

U.S. PATENT DOCUMENTS

| | | | |
|---|---|---|---|
| 8,654,319 B2* | 2/2014 | Rao | G01N 21/532 |
| | | | 356/73.1 |
| 9,453,798 B2* | 9/2016 | Banks | G01N 35/08 |
| 9,612,221 B2* | 4/2017 | Xiao | G01N 27/27 |
| 9,869,613 B2* | 1/2018 | Hausot | A61M 5/14276 |
| 10,408,040 B2* | 9/2019 | Angelescu | G01N 11/02 |
| 11,613,458 B2* | 3/2023 | Grose | B67D 7/62 |
| | | | 141/1 |
| 11,725,972 B2* | 8/2023 | Grose | B67D 7/221 |
| | | | 73/149 |
| 2018/0099860 A1* | 4/2018 | Bjornebo | G01N 33/22 |

* cited by examiner

HYDROCARBON CONDENSATE DETECTION AND CONTROL

CROSS-REFERENCE TO RELATED APPLICATIONS

The present application is a continuation-in-part of U.S. utility patent application Ser. No. 17/091,800, filed Nov. 6, 2020, which claims priority to U.S. Provisional Patent Application No. 62/978,015, filed Feb. 18, 2020, and which claims priority to U.S. Provisional Patent Application No. 63/034,945, filed Jun. 4, 2020, and which is a continuation-in-part of U.S. utility patent application Ser. No. 17/024,673, filed Sep. 17, 2020, which claims priority to U.S. Provisional Patent Application No. 63/022,351, filed May 8, 2020. The present application is also a continuation-in-part of the aforementioned U.S. utility patent application Ser. No. 17/024,673, filed Sep. 17, 2020. All of the aforementioned applications are incorporated herein in their entireties.

BACKGROUND

Field of the Disclosure

The present disclosure relates generally to detection of condensed hydrocarbons and particularly detecting hydrocarbon condensate in impaired fluids from oil and gas fracturing.

Description of the Related Art

Natural gas production methods produce a variety of constituent materials, often including hydrocarbons that condense into liquids under ambient conditions. Those condensed hydrocarbons, often referred to as condensates in oil and gas field vernacular, pose a danger to handlers who are not aware of their presence because such hydrocarbon condensates can easily burn or explode when they exist in significant quantities. Hydrocarbon condensates are also valuable for use in various chemical processes.

A significant safety concern is condensate accumulation in fracking water. A ramification of undetected condensate impinging upon fracking sites and trucking assets used in fracking operations is the danger of explosion. Early catastrophic accidents experienced in basins across the United States can be directly correlated to condensate encroachment—that is, condensate ended up being in areas where it never should have been.

Condensate can be produced as part of a well's natural lifecycle throughout the production phase of natural gas wells, particularly in wet gas producing wells. Production fluid gathering systems are generally constructed on well locations to store both production water and condensate that is gathered through the normal production cycle. The production water and hydrocarbons striate within the production tank infrastructure to allow for water haulers to haul production water for reuse or disposal, and hazardous material haulers to haul condensate to separation facilities for marketing.

While operational procedures can be implemented with a goal to prevent the hauling of flammable liquids by non-sanctioned haulers, errors including those relating to faulty telemetry or operational oversight can lead to potentially unsafe conditions. In January of 2003, a truck fire erupted that resulted in three people being seriously burned and two people being killed. The cause of the fire was determined to be condensate contamination of non-flammable liquid that was caused by the release of hydrocarbon vapor during the unloading process. This accident could have been prevented if the condensate were observable and detected before it was improperly released. There are many other examples of dangerous incidents that have occurred in the past, and these types of incidents continue to have catastrophic potential across gas producing basins.

The problem of condensate migration into unwanted operational areas is further compounded when production water is reused for completion operations. Centralized water offload locations designed to reuse water from well sites create a more functional platform for operational water reuse. Troublingly, such water reuse operations create opportunities for production water combined with condensate to be offloaded into centralized facilities, contaminating the bulk water and requiring costly cleanup efforts.

Accordingly, there is a need to detect hydrocarbon condensate.

There is also a need to prevent hydrocarbon condensate from being transferred to tanks and other vessels and locations that are not equipped to handle hydrocarbon condensate.

There is also a need to provide a warning when there is a dangerous level of hydrocarbon condensate in water or an aqueous mixture of water and other substances, such as production water used in a drilling site.

There is also a need to separately collect hydrocarbon condensate that is present with other materials. That hydrocarbon condensate may be collected to improve the safety of the other material, to make the hydrocarbon condensate useful, or both.

Accordingly, the present invention provides solutions to the shortcomings of storing and hauling substances that may contain hydrocarbons that may condense out of the substances and provides detection of such hydrocarbons. Those of ordinary skill in the art will readily appreciate, therefore, that those and other details, features, and advantages of the present invention will become further apparent in the following detailed description of the preferred embodiments of the invention.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

SUMMARY OF THE INVENTION

In an embodiment, a hydrocarbon detection and control system for an aqueous mixture includes a controller, a fluorometer, a color sensor, a turbidity sensor, and a control device. The controller has a plurality of inputs to which the fluorometer, the color sensor, and the turbidity sensor are attached and the controller has at least one output to which the control device is coupled. The fluorometer senses hydrocarbon fluorescence in an aqueous mixture and provides a signal to the controller commensurate with an amount of hydrocarbons in the aqueous mixture. The color sensor provides a signal commensurate with aqueous mixture color to the controller. The turbidity sensor provides a signal to the controller commensurate with turbidity of the aqueous mixture. The control device modifies flow of the aqueous mixture.

In another embodiment, a multi-input pipeline hydrocarbon detection and control system is provided. The multi-input pipeline hydrocarbon detection and control system includes a plurality of pipelines, each to receive aqueous process fluid from a single separate unloading station and discharge that aqueous process fluid into a common manifold pipeline. Each unloading station has a processor that contains instructions which, when executed by the processor, cause the processor to receive a fluorescence signal from a fluorometer at a first input, the fluorometer to sense hydrocarbon fluorescence in an aqueous process fluid and the fluorescence signal indicating an amount of hydrocarbon content in the aqueous process fluid; receive a color signal from a color sensor at a second input, the color sensor to sense the color of the aqueous process fluid and the color signal indicating the color of the aqueous process fluid; receive a turbidity signal from a turbidity sensor at a third input, the turbidity sensor to sense turbidity of the aqueous process fluid and the turbidity signal indicating the turbidity of the aqueous process fluid; and transmit a control signal to a control device coupled to an output, the control device to modifying flow of the aqueous process fluid.

A method of detecting hydrocarbon in an aqueous mixture and controlling flow of that aqueous mixture is also provided. That method includes receiving a fluorescence signal from a fluorometer sensing hydrocarbon fluorescence in an aqueous mixture, receiving a color signal from a color sensor sensing the color of the aqueous mixture, receiving a turbidity signal from a turbidity sensor sensing turbidity of the aqueous mixture, receiving a turbidity signal from a turbidity sensor sensing turbidity of the aqueous mixture, and controlling the flow of the aqueous mixture based on the hydrocarbon content of the aqueous mixture.

Other embodiments, which may include one or more portions of the aforementioned apparatuses and methods or other parts or elements, are also contemplated, and may have a broader or different scope than the aforementioned apparatuses and methods. Thus, the embodiments in this Summary of the Invention are mere examples, and are not intended to limit or define the scope of the invention or claims.

DETAILED DESCRIPTION

The following description is provided to enable those skilled in the art to make and use the described embodiments contemplated for carrying out the concept. Various modifications, equivalents, variations, and alternatives, however, will remain readily apparent to those skilled in the art. Any and all such modifications, variations, equivalents, and alternatives are intended to fall within the spirit and scope of the present concept.

Any reference in the specification to "one embodiment," "a certain embodiment," or a similar reference to an embodiment is intended to indicate that a particular feature, structure or characteristic described in connection with the embodiment is included in at least one embodiment of the invention. The appearances of such terms in various places in the specification do not necessarily all refer to the same embodiment. References to "or" are furthermore intended as inclusive, so "or" may indicate one or another of the ored terms or more than one ored term.

Figure 1:
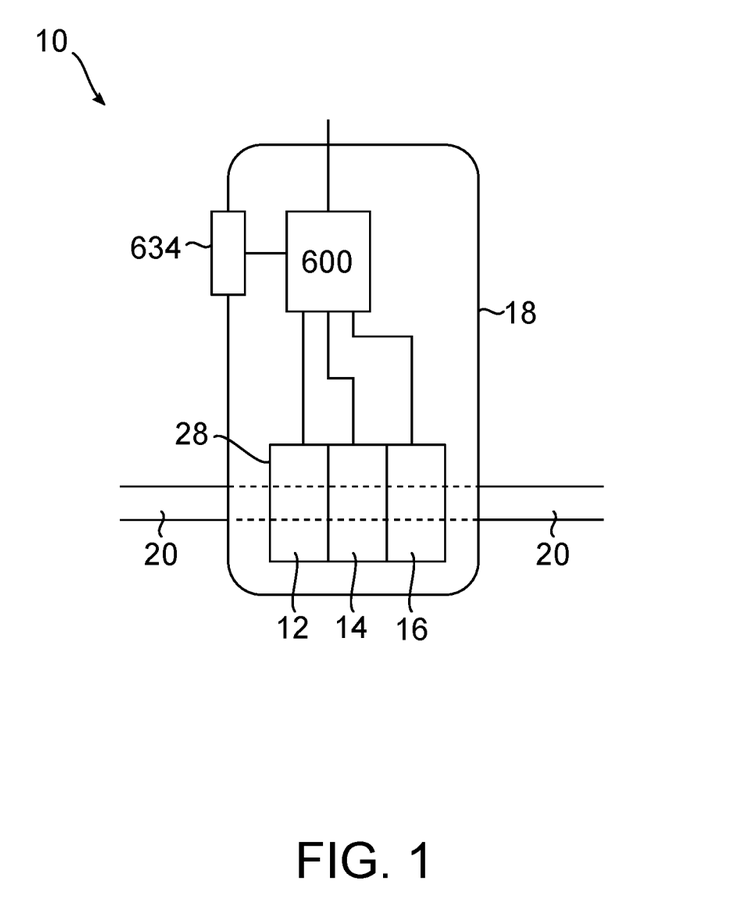
FIG. 1 illustrates an embodiment of a hydrocarbon detection and control system.

FIG. 1 illustrates an embodiment of a hydrocarbon condensate detection system 10. The hydrocarbon detection system of FIG. 1 includes a fluorometer 12 to measure the concentration of hydrocarbons in a fluid, a turbidity sensor 14 to measure an extent of suspended solids in the fluid, a color sensor 16 to measure the color of the fluid, and a controller 600 to receive signals from the fluorometer 12, turbidity sensor 14, and color sensor 16 and to provide an output based on the presence of significant hydrocarbons in the fluid. The sensors 12, 14, and 16 may be disposed in a line 20 through which an aqueous mixture flows.

Figure 5:
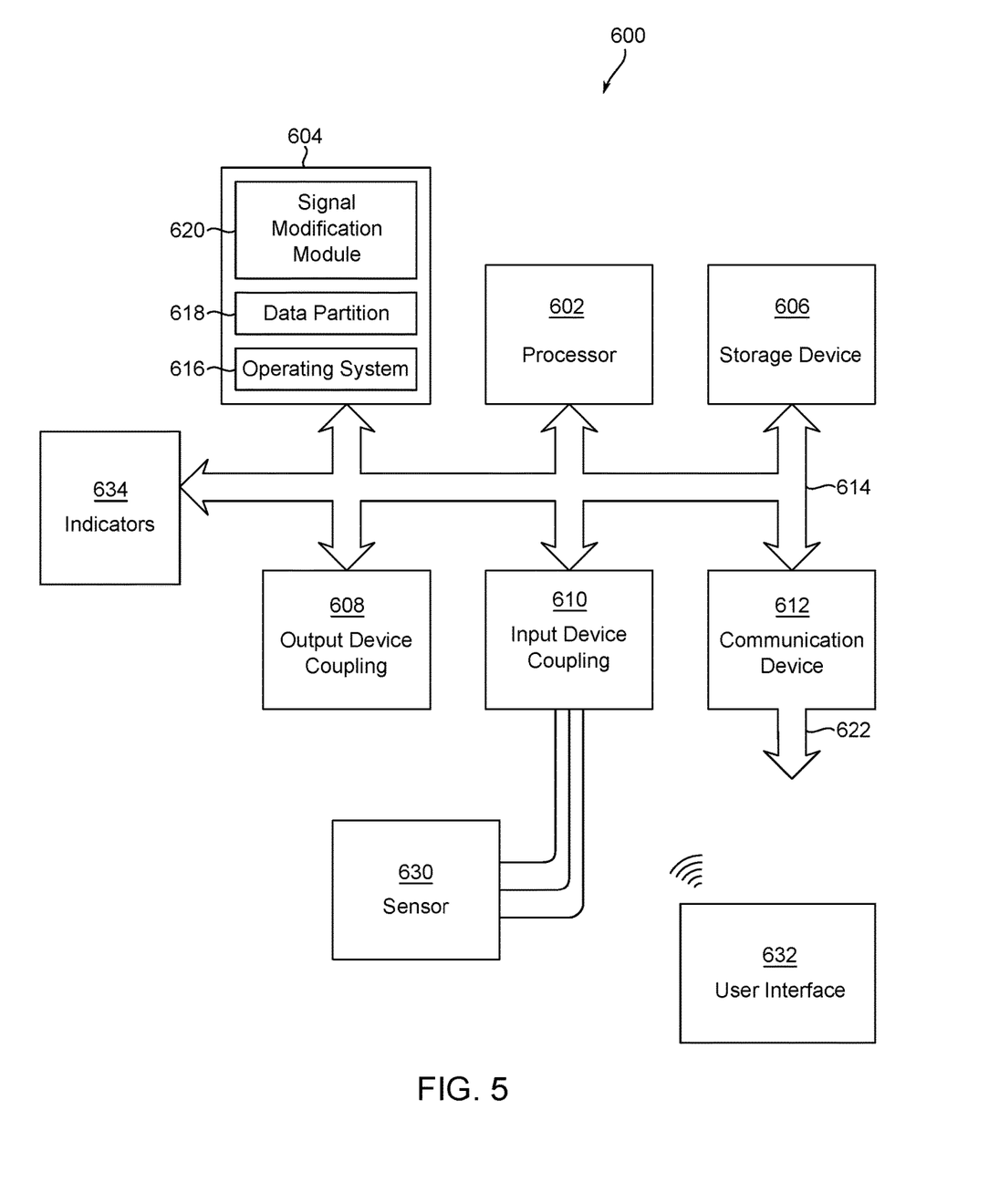
FIG. 5 illustrates an embodiment of a processor-based controller for use in a hydrocarbon condensate detection system.

The fluorometer 12, turbidity sensor 14, and color sensor 16 are coupled to inputs of a processor-based control device, such as the controller 600 illustrated in FIG. 5 or a microprocessor that may be packaged with the sensors 12, 14, 16 as a unit. The sensors provide a signal to the controller 600 that is commensurate with the amount of hydrocarbons in the aqueous mixture for the fluorometer 12, commensurate with turbidity of the aqueous mixture for the turbidity sensor 14, and commensurate with aqueous mixture color for the color sensor 16. The controller 600 furthermore controls the flow of an aqueous mixture flowing past the fluorometer 12, turbidity sensor 14, and color sensor 16 through a flow control output, to modify flow of the aqueous mixture when hydrocarbon content of the aqueous mixture reaches one or more levels, such as a shutdown level that may be predetermined. A hysteresis may be provided to return to the original flow pattern when hydrocarbon content of the aqueous mixture returns to a desired level, which may be predetermined and may be offset from the shutdown level. The flow control output may be any desired output, for example an analog or digital signal that accomplishes flow control. The fluorometer 12, turbidity sensor 14, color sensor 16, or a sensor package 28 comprising a combination of those sensors 12, 14, and 16 may also provide a 4 mA or other desired signal as a sensor operational output that may indicate that the sensors are working properly or indicate that one or more of the sensors has become dirty or is otherwise not properly sensing hydrocarbons.

The aqueous mixture may be a mixture that is used in a shale fracturing or fracking operation and may be referred to as production water or impaired water. Fracking may refer to an operation employed to extract desired materials, such as natural gas or oil, from shale or other geological formations. Such a fracking production water aqueous mixture may include water, sand, and various compounds intended to aid in the flow of natural gas, oil, or other desired materials from the shale.

Hydrocarbons, such as those included in natural gas and oil, are generally separated from the aqueous mixture, but some hydrocarbons may bypass the separation process and can be mixed with or layered with the fracking aqueous mixture. Those hydrocarbons can be valuable when separated from the fracking aqueous mixture, but can be dangerous when found with the fracking aqueous mixture. For example, a tank of fracking aqueous mixture without hydrocarbons may be safely handled or transported and may be used in another fracking site or other operation, while a tank that contains hydrocarbons with the aqueous mixture may be a fire or explosion danger, particularly when it is unknown that the tank includes hydrocarbons and is not handled with the care to be taken for a tank containing hydrocarbons.

Hydrocarbons generally have a different fluorescence than water or an aqueous fracking mixture. Accordingly, the fluorometer 12 of this invention can be used to sense hydrocarbons in water and aqueous mixtures, including fracking aqueous mixtures. In an embodiment in which hydrocarbons are to be sensed in an aqueous mixture, the fluorometer is arranged to sense hydrocarbon fluorescence. A level of hydrocarbon content may be set in the control device (e.g., 600) and if hydrocarbon fluorescence reaches a predetermined level, as sensed by the fluorometer 12 in the aqueous mixture, the controller (e.g., 600) may initiate an action, such as providing an alarm to an operator or attendant, closing a valve through which the aqueous mixture is flowing, or diverting flow of the aqueous mixture to a different tank or location. Hydrocarbon sensing may, for example, be performed in units of parts per million, parts per billion, or another level of hydrocarbon molecules or units suspended in the fluid or an amount of hydrocarbon present per unit of aqueous mixture.

Hydrocarbons may fluoresce differently in fluid of certain colors and in fluids containing certain suspended solids or quantities of suspended solids. Accordingly, turbidity, or a quantity of suspended solids in the fluid, and color of the fluid, are sensed in certain hydrocarbon sensing embodiments disclosed herein and the resulting turbidity and color may be used to filter the sensed fluorescence to remove inaccuracies in sensed fluorescence caused by turbidity and color, and thereby to acquire a more accurate fluorescence and a more accurate determination of hydrocarbon content of the fluid.

Further with regard to hydrocarbon fluorescence in turbid aqueous mixtures, hydrocarbons may not fluoresce as well or may fluoresce excessively in fluid with high turbidity, or with an excessive amount of solid matter carried in the fluid, as they would in clean water. To correct hydrocarbon sensing by fluorescence, a turbidity sensor may emit light in the red (i.e., 610-800 nm) or infrared (i.e., >800 nm) ranges and measure the scattering of light from suspended particles to determine turbidity of the aqueous mixture and as a filter to hydrocarbon content determination. Thus, the effect of turbidity on hydrocarbon fluorescence may be taken into account when determining hydrocarbon content of the aqueous mixture.

Also, with regard to hydrocarbon fluorescence in colored aqueous mixtures, hydrocarbons may not fluoresce as well or may fluoresce excessively in fluid of certain colors. To correct hydrocarbon sensing by fluorescence, a color sensor may measure the color of the aqueous mixture and the hydrocarbon content determination may take the effect of color on hydrocarbon fluorescence into account when determining hydrocarbon content of the aqueous mixture.

The sensors 12, 14, and 16 may be combined in a sensing package 28, partially combined, or separate, and certain sensors (e.g., turbidity sensor 14 and color sensor 16) may not be employed in certain circumstances where, for example, turbidity or color are not significant factors in hydrocarbon fluorescence. In many applications, however, the color and turbidity properties of the aqueous mixture are of interest in measuring or calculating concentrations of hydrocarbons in an aqueous mixture to compensate for fluctuations in the fluorescence measurement made by the fluorometer 12. A sensor housing 18 may furthermore include the fluorescence sensor 12, the turbidity sensor 14 and the color sensor 16 and additional components that are not used in a fluorescence determination, but that are nonetheless incorporated into the single probe housing 18 to simplify installation or to assure that all sensing is taking place in the same vicinity.

Figure 2:
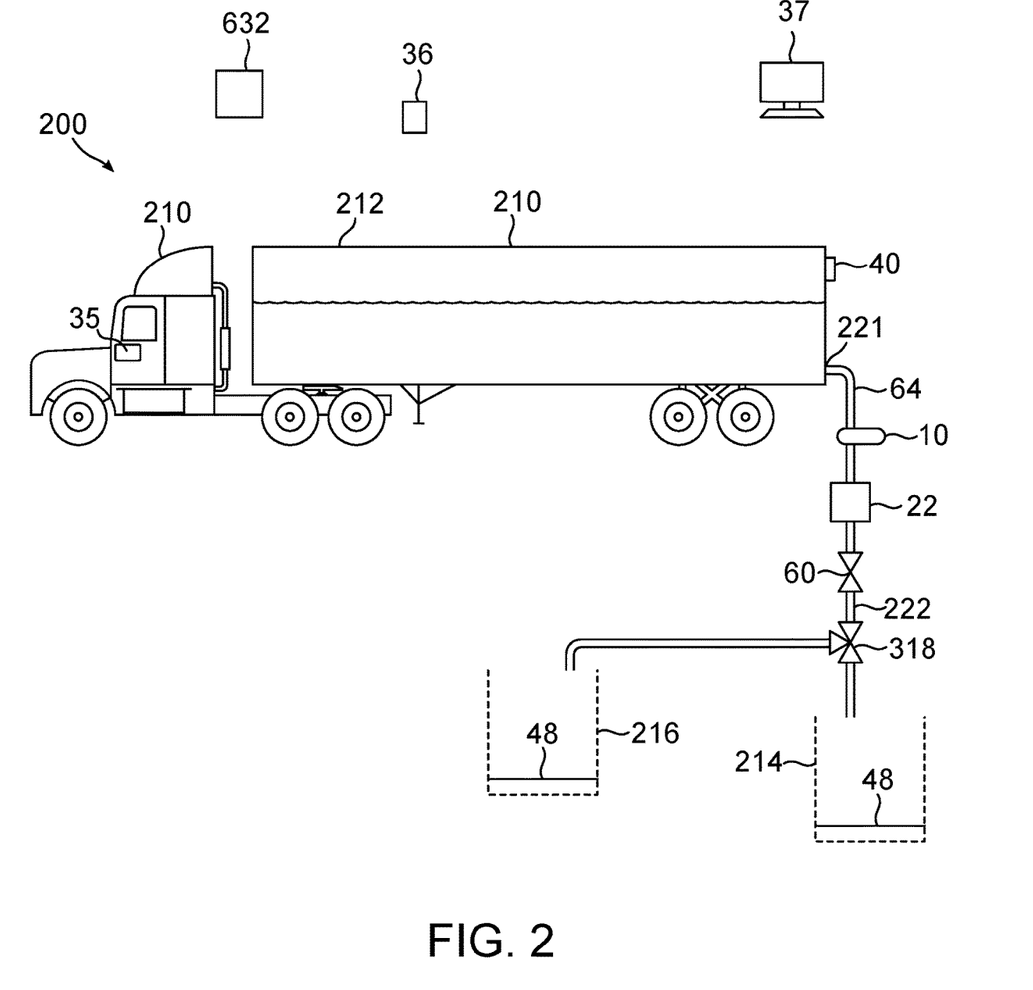
FIG. 2 illustrates an embodiment of an aqueous fluid transfer system employing a hydrocarbon detection and control system.

Hydrocarbon content may be sensed in a variety of locations, including pipelines, transfer hoses 64, and tanks 212, 214, and 216. Where hydrocarbon sensing is performed outdoors and the sensors 12, 14, 16, sensor unit, 28, or complete hydrocarbon detection and control system 10 is installed outdoors, protections may be provided to protect the outdoor equipment, including static protection and lightening protection.

FIG. 2 illustrates an embodiment of an aqueous fluid transfer system 200 employing a hydrocarbon detection and control system 10 installed in or attached to a tanker truck 210 outlet 221, a line 222 leaving the tanker truck 210 and entering one or more holding tanks 214 or 216, or otherwise as desired to sense hydrocarbon mixed with the aqueous fluid. In that embodiment, an aqueous mixture is hauled to a drilling site or another site where the aqueous mixture is needed or to be stored. The aqueous mixture is hauled in the tank 212 of the tanker truck 210 in the embodiment illustrated in FIG. 2. Transfer may begin with a transfer hose 64 acting as the line 222 extending from the truck tank 212 to the aqueous mixture holding tank 214 or 216. The hydrocarbon detection system 10 may be installed in the line 222, coupled to the truck 210 at the inlet of the line 222 or transfer hose 64, or otherwise situated such that the aqueous mixture passes the hydrocarbon detection system 10 as it flows from the truck tank 212 such that the hydrocarbon detection system 10 senses hydrocarbon content in the aqueous mixture leaving the tank 212 of the tanker truck 210.

Aqueous mixture transfer from a truck 210 tank 212 typically begins with transfer of aqueous mixture 48 into the aqueous mixture tank 214. If hydrocarbon content of the aqueous mixture leaving the truck tank 212 exceeds a predetermined limit, as sensed by the hydrocarbon detection system 10, the hydrocarbon detection system 10 takes action to stop transfer of the aqueous mixture 48 to the aqueous mixture holding tank 214. For example, in embodiments, if a hydrocarbon content of the transferring aqueous mixture 48 being sensed by the hydrocarbon detection system 10 exceeds 800 ppm, the hydrocarbon detection system stops flow of the aqueous mixture 48 by de-energizing a pump 22, closing a valve 60, actuating a diverting valve 318, de-energizing a compressor providing pressure to the truck tank 212, or de-energizing a vacuum creating device that draws the aqueous mixture from the tank 212. Alternatively, the hydrocarbon detection system 10 may provide an audible or visual alarm 40 or otherwise notify an operator that the hydrocarbon level of the aqueous mixture 48 is too high for transfer to continue into the aqueous mixture holding tank 214 or that hydrocarbon content of the aqueous mixture 48 is otherwise out of range. The hydrocarbon detection system 10 or an operator may alternatively, or in addition, divert the aqueous mixture 48, redirecting the aqueous mixture from, for example an aqueous mixture reservoir, to another location, such as a hydrocarbon and aqueous mixture reservoir or a hydrocarbon condensate tank 216 when excess hydrocarbon content is sensed in the aqueous mixture 48. For example, the hydrocarbon detection system 10 may divert the flow of aqueous mixture 48 by actuating a diverting valve 318 or one or more two-way valves, such that the aqueous mixture 48 is transferred to the condensate tank 216 rather than the aqueous mixture tank 214. Where no diverting valve 318 is employed, the flow of aqueous mixture 48 from the truck 210 tank 212 to the aqueous mixture holding tank 214 may be terminated and the line 222 or transfer hose 64 may be moved to the hydrocarbon condensate tank 216 such that transfer of aqueous mixture from the truck 210 tank 212 may continue.

Valves 60, 318 may include fast acting pneumatic or electric valves that, upon detection of condensate levels of a predetermined hazardous PPM range, can quickly stop or redirect flow. Redirection of the flow of aqueous mixtures containing excess hydrocarbons can allow for the capture and separation of hydrocarbon condensate in one or more separate process vessels to eliminate safety hazards while allowing for the resale of the captured hydrocarbons.

In an embodiment of the hydrocarbon detection system 200 of FIG. 2, an operator pulls a truck 210 into the vicinity of a fracking water, aqueous mixture tank 214. Information about the truck 210 is communicated to a site controller, either automatically or upon initiation by the driver or an operator. An operator then connects the tank 212 of the tanker truck 210 to a fracking water aqueous mixture tank 214 for transfer of aqueous mixture.

Figure 3:
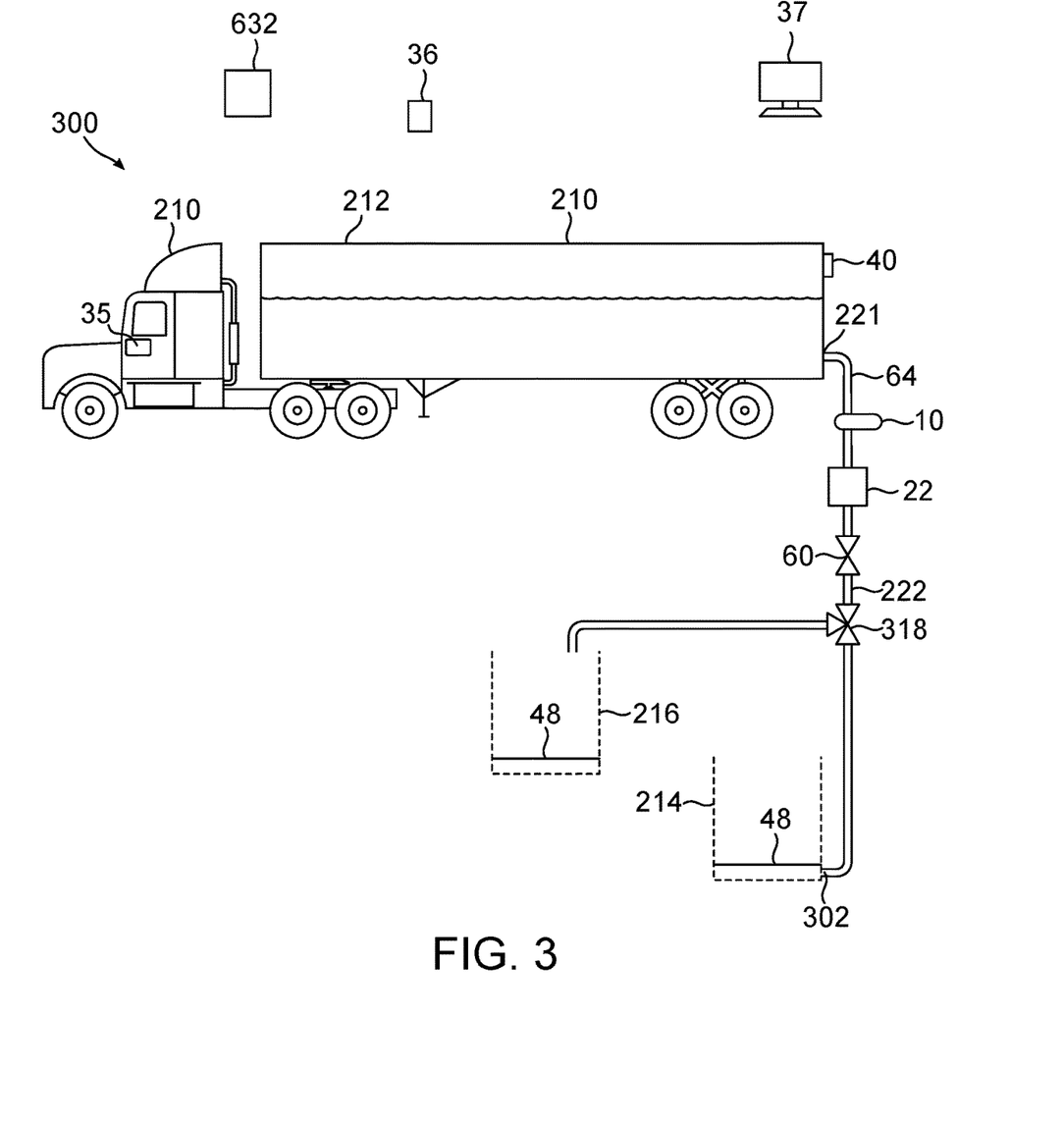
FIG. 3 illustrates another embodiment of an aqueous fluid transfer system employing a hydrocarbon detection and control system.

FIG. 3 illustrates an embodiment 300 in which aqueous mixture transfer from an aqueous mixture tank 214 to a truck 210 tank 212 may be accomplished using the hydrocarbon detection system 10. In that embodiment, transfer of aqueous mixture to the truck 210 tank 212 is halted if a hydrocarbon content higher than desired is sensed in aqueous mixture being transferred to the truck 210 tank 212 using any of the processes described in connection with the aqueous mixture transfer described in connection with FIG. 2. In such an embodiment, the hydrocarbon detection system 10 may be placed anywhere in the line 222, whether the line 222 is a transfer hose 64, solid pipe, a manifold system, or a combination of such elements. The hydrocarbon detection system 10 may, for example, be located in an aqueous mixture tank 214 outlet 302 that leads to the truck 210 tank 212. If the hydrocarbon detection system 10 senses a level of hydrocarbons above its predefined setting or limit, truck 210 tank 212 loading will be stopped by valve, pump de-energization, operator, or as described elsewhere herein. High hydrocarbon (also referred to as hydrocarbon condensate or simply condensate) content aqueous mixture may be diverted to a condensate tank 216 or another location. Hydrocarbons may further be removed from the high hydrocarbon aqueous mixture for sale or other use and the aqueous mixture may be used after the hydrocarbons are removed.

In an embodiment, aqueous mixture containing a high hydrocarbon content may be left to settle and separate in the condensate tank 216. When settled, the hydrocarbons will generally separate from the aqueous mixture with hydrocarbons floating above or on top of the aqueous mixture. Once settled, the aqueous mixture may be drawn from the bottom of the condensate tank 216 and moved to a truck 210 tank 212 or aqueous mixture tank 214 for further use. Alternatively or in addition, the hydrocarbon condensate may be drawn from the hydrocarbon condensate tank 216 for use elsewhere.

Figure 4:
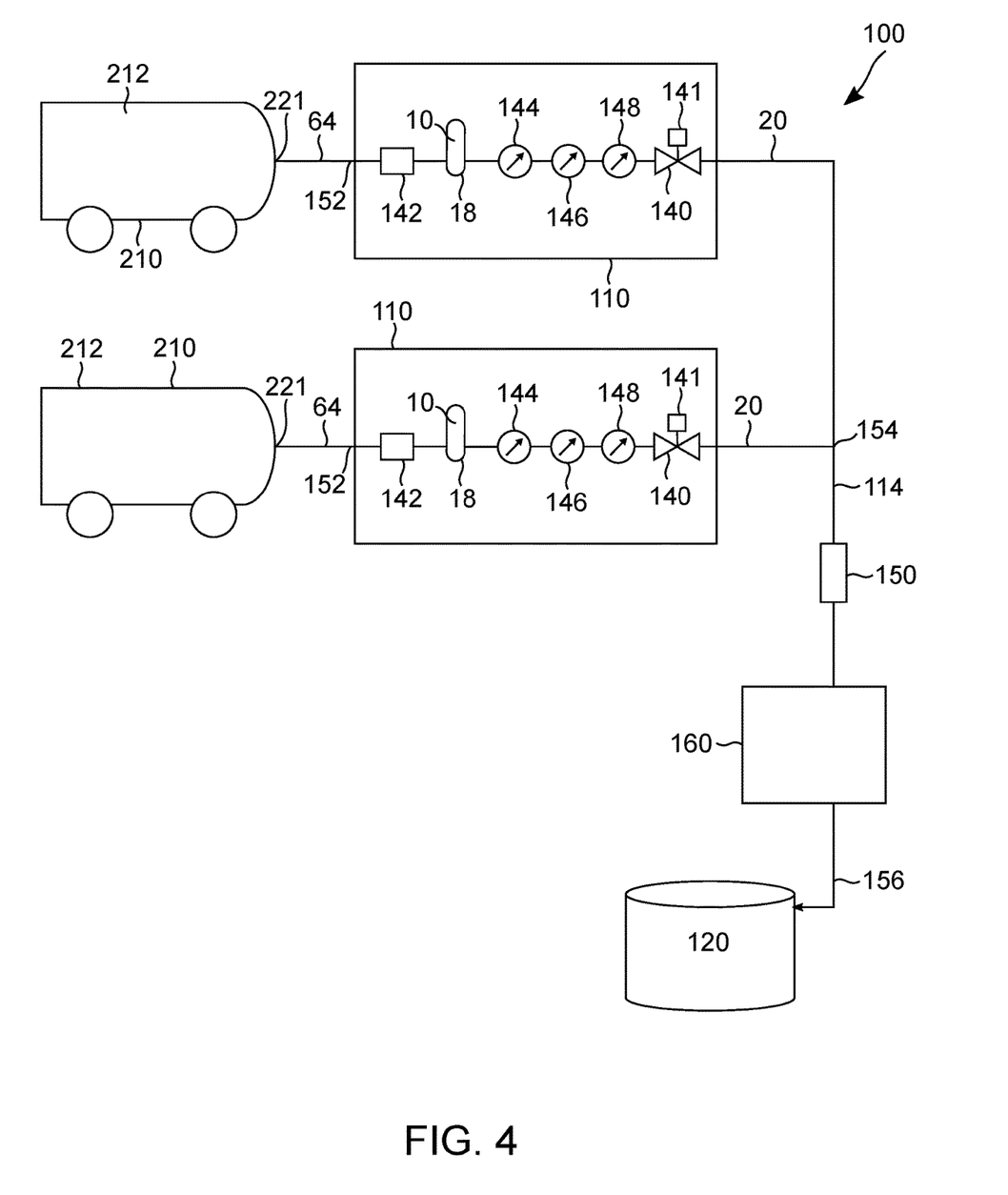
FIG. 4 illustrates an embodiment of a plurality of hydrocarbon condensate detection systems deployed in a manifold pipeline fluid transfer system.

FIG. 4 illustrates an embodiment of a plurality of hydrocarbon condensate detection systems 10 deployed in a manifold pipeline fluid transfer system 100 through which an aqueous mixture flows and, in certain embodiments, is propelled. In the embodiment illustrated in FIG. 4, one hydrocarbon detection system 10 of FIG. 1 is installed in each line 20 through which an aqueous process fluid flows. Those hydrocarbon detection systems 10 sense hydrocarbons flowing in the process fluid. In the embodiment illustrated, two unloading stations 110 are provided, though any number of stations desired may be included in a manifold pipeline fluid transfer system 100. A truck 210 tank 212 may be coupled to each unloading station 110, for example, by way of a separate transfer hose 64 for each truck 210 tank 212. Each unloading station 110 includes a hydrocarbon sensing package 28 and controller 600 that may include a combined fluorescence, turbidity, and color sensor hydrocarbon detection system 10. Each unloading station 110 may also include a variety of sensors, valves, gauges, and displays, such as an offloading valve 140, a sight tube 142, a pressure gauge or sensor 144, a flow gauge or sensor 146, a temperature gauge or sensor 148, or any other desired gauge or sensor. For the purpose of the embodiment illustrated in FIG. 4 gauges may provide a visual representation of a characteristic of the fluid in the offloading portion of the line 20 or pipe, and a sensor or sensors may provide signals that represent a fluid characteristic to a processor-based device, such as the controller 600 illustrated and discussed in connection with FIG. 5 or a control system or other computing device. Sensor signals may, furthermore, be transmitted through wires or wirelessly.

The manifold pipeline fluid transfer system 100 of this embodiment may be employed to expedite offloading of tanker trucks 210 while stopping unloading when high or dangerous hydrocarbon content is sensed in the aqueous mixture being unloaded. In the embodiment illustrated in FIG. 4, a plurality of tanker truck 210 offloading stations 110 are provided so that more than one tanker truck 210 can have fluid from their associated tanks 212 offloaded simultaneously into the manifold. For example, in an embodiment for offloading tanks of water-based fluids used in hydraulic fracturing, ten offloading stations 110 may be provided. A tanker truck 210 may pull up to and connect to the manifold pipeline fluid transfer system 100 through an offloading station 110 when that offloading station 110 is not occupied or otherwise used by another truck 210. An offloading station 110 can be used independent of other station occupancy, regardless of any use or maintenance occurring of the other offloading stations 110, and regardless of whether one or more trucks 210 occupying one or more other stations are in the process of offloading. The tanker truck 210 that pulls into an offloading station can connect to an offloading portion of the line 20 at the offloading station 110 and offload the contents of its tank 212 through the offloading portion of the line 20 or pipe while other trucks 210 are simultaneously offloading their tanks 212.

In certain embodiments, each offloading station 110 includes a flexible transfer hose hook-up 152 through which fluid from the tank 212 of the truck 210 can flow into a manifold 114 and from there, directly or indirectly, into a site tank 120. The manifold 114 may be in fluid communication with each offloading station 110 and the site tank 120. The manifold 114 may be a piping system that accepts fluid from each offloading station 110, combines fluid received from the offloading stations 110 at one or more junctions 154, and deposits the fluid received from the offloading stations 110 into the site tank 120.

The manifold pipeline fluid transfer system 100 may be configured in various ways that are suited to an offloading site. The manifold pipeline fluid transfer system 100 illustrated in FIG. 4 includes a plurality of lines 20 that flow through offloading stations 110 into a manifold 114 branch extending to each offloading station 110. The plurality of lines 20 extending from the offloading stations join at one or more junctions 154 to a common manifold 114 that extends to a tank such as an aqueous mixture storage tank 120 illustrated in FIG. 4. The common line 156 may alternatively extend to any desired destination into which the fluid from the truck 210 tanks 212 is desired to be deposited, including, for example, a storage vessel of any type, an underground storage area, a well, or a rig of some type, such as a drill rig.

A flow sensor or meter 150 or another flow measuring device may be placed in the manifold 114 common line to measure the total flow through the manifold 114. That flow measurement may be used to determine total flow into the manifold 114 and may be used to control flow into the manifold 114, for example, through the offloading valves 140. Alternatively, a flow switch may be placed in the manifold 114 common line to indicate fluid is flowing through the manifold 114. Either the flow meter 150 or switch may be coupled to a computerized monitoring or control system including the processor-based control device 600 illustrated and discussed in connection with FIG. 5.

The offloading valves 140 may be located in each offloading station 110 to control or flow from the offloading stations 110 or to isolate one or more offloading stations 110, for example when high hydrocarbon content is sensed in the aqueous mixture flowing into that offloading station 110. The offloading valves 140 may be a variety of types of valves, including a ball valve, a gate valve, or a globe valve. The offloading valve 140 may furthermore be actuated manually, may be automatically controlled for full opening or closure, or may be modulated for regulated flow by a manifold control system, such as the controller 600 illustrated in FIG. 5. The offloading valve 140 may be of a size that permits full flow of fluid from the truck 210 tank 212, such as a 4" valve with a full flow characteristic. The full flow characteristic of a ball valve, for example, may be beneficial to enable fast offloading of tanks 212 coupled thereto. Alternatively, the offloading valve 140 may be configured with a linear control characteristic, such as that provided by a globe valve, or may have another desired flow characteristic. The offloading valve may furthermore be used to permit flow through the offloading station 110 when open and to prevent flow into the offloading station 10 when closed.

Control of the offloading valve 140 and other components of the manifold system 100 may be performed using a computer, such as the processor-based controller 600 illustrated and discussed herein in connection with FIG. 5.

Fluid unloaded from a tanker truck 210 is known to sometimes encounter gas, particularly air, mixing with the fluid. Thus, an air removal system 160 may be provided in the manifold system 100.

In an embodiment in which an offloading valve 140 is included in the unloading station 110, the offloading valve 140 is opened when the transfer hose 64 is attached to the unloading station 110. The hydrocarbon detection and control system 10 is coupled to an actuator 141 on the offloading valve 140 and the actuator 141 closes the offloading valve 140 when a hydrocarbon limit set in the hydrocarbon detection and control system 10 exceeds its preset limit, which may be 800 ppm of hydrocarbons in the aqueous mixture flowing past the hydrocarbon detection and control system 10.

It may be seen that in a manifold pipeline fluid transfer system 100 having multiple stations, while not necessary, it may be beneficial to have a separate hydrocarbon detection and control system 10 and offloading valve 140 at each station so that when the hydrocarbon limit is exceeded at one station, aqueous mixture flow through that station may be stopped while trucks 210 may continue to offload aqueous mixture at the remaining stations.

In operation, the sensors 12, 14, and 16 portion of a hydrocarbon detection and control module 10 may be installed in a line, such as a pipe carrying the fluid for which hydrocarbon detection is desired. Installation of the sensors may be by insertion of the sensors 12, 14, and 16 into the line 20 and affixing the sensors 12, 14, and 16 in the line 20. A pump 22 may propel the fluid through the line 20, or the fluid may flow by way of gravity or other means. A flow sensor 150 may also be included in the line 20 and a pressure sensor 144 or other sensors may also or alternatively be included in the line 20.

Flow shut-off devices may be included in the line 20, including a pump shutoff control and one or more valves, which may be used to isolate a section of the line 20 into which one or more of the sensors 12, 14, and 16 are inserted.

The hydrocarbon detection and control module 10 may have its sensors 12, 14, and 16 encapsulated in a probe housing 18 that may be inserted into the line 20. The hydrocarbon detection and control module 10 may provide continuous monitoring of the fluid stream and may have an accuracy of a single PPM of hydrocarbon.

The hydrocarbon detection and control system 10 may be housed in a Class1/Div2 or Class1/Div1 enclosure for deployment in hazardous areas or another desired enclosure, and the hydrocarbon detection and control system 10 may be outfitted with a self-cleaning function tailored to the water stream to ensure that it does not lose detection ability due to plating or fouling. The hydrocarbon detection and control system 10 may be powered by a nominal 110 VAC power supply or another desired electrical power supply.

The hydrocarbon detection and control system 10 may also include a sensor cleaning system to remove hydrocarbons, solid impurities, or other foreign materials from the fluorescence, color, and turbidity sensors 12, 14 and 16. In an embodiment, that cleaning system may draw 1 HP of power and create 7 CFM of airflow across the sensors 12, 14, and 16 at 90 psi per hour.

In certain embodiments, the hydrocarbon detection and control system 10 may include cellular or satellite connectivity so that the system can be accessed from anywhere in the world allowing for visibility into condensate concentrations and alarm conditions.

Regarding identification provided when a tanker truck 210 approaches a site, such as an offloading site or an onloading site, the truck 210 or tank 212 may be identified by any unique identifier of the tank 212 or the truck 210 on which a particular tank 212 is mounted and may be recognized in a variety of ways. For example, a user interface may be used to identify the tank 212 currently in position to operate (e.g., load or unload) by way of a wired or wireless transmission from an electronic device associated with the tank 212. A unique identifier may be transmitted from the tank 212 or associated truck 210 by any signal transmitting device, or an identifier may be read and transmitted by a geofencing or other position determination device that senses the presence of the tank 212 or its associated truck 210. Alternatively, a driver or operator may enter the tank identifier into a device to recognize a tank 212 that is currently under operation.

In an embodiment, a tanker truck driver will carry an electronic fob 36 or other device that contains a name or an identification of the driver, the company that operates the truck 210, a truck 210 identifying number, or any other tanker truck 210 related information desired, such as a quantity of aqueous mixture carried by the truck tank 212 or a capacity of the tank 212, and transmits that identification to an appropriate communicating node at, or remote from, the site.

FIG. 5 illustrates an embodiment of a processor-based controller 600 for use in a hydrocarbon condensate detection system. The processor-based controller 600 may, for example, be a microcontroller, an application specific integrated circuit, a general-purpose computer, or a programable logic controller, such as those manufactured by Rockwell International under the Allen Bradley trademark. In the embodiment illustrated in FIG. 5, the processor-based device 600 includes a processor 602 and a communication device 612. The processor 602 and communication device 612 can be combined in a microprocessor or other device and other components (e.g., 604 and 606) may also be included in such a microprocessor or other device.

The communication device 612 may be wired to a device to which it communicates. The communication device 612 may, in addition or alternatively, wirelessly communicate with one or more devices over a network 240, which may be a wireless network, such as a mobile smartphone network, a short-range wireless protocol, such as Bluetooth or Zigbee, or another desired communication protocol, such and the communication device 612 may operate both wired and wirelessly. The processor-based device 600 may furthermore include memory 604, an input 610 that may receive an input signal, such as a signal transmitted by a sensor, and an output 608 that may transmit a control signal, instruction, or data to another device, such as a valve actuator or other controlled device. The output device may alternatively or in addition provide a reading, for example a current quantity of hydrocarbons present in the aqueous mixture flowing past one or more hydrocarbon sensors.

The processor-based device 600 may also be coupled to a user interface 632 to receive one or more signals from, for example, one or more of a keyboard, touch screen, mouse, microphone or other input device or technology and may have associated software. The user interface 632 may also transmit information to, for example, a printer or screen coupled to the user interface 632 or the output 608.

The memory 604 may, for example, include random-access memory (RAM), flash RAM, dynamic RAM, or read only memory (ROM) (e.g., programmable ROM, erasable programmable ROM, or electronically erasable programmable ROM) and may store computer program instructions and information. In embodiments, the memory 604 may be partitioned into sections including an operating system partition 616 where system operating instructions are stored, a data partition 618 in which data, such as total hydrocarbon passage and total aqueous mixture passage may be stored, and a signal modification module 620 that may be used to convert sensor signals into human readable engineering units.

The storage device 606 may include a memory device or a data storage device or a combination of both memory and data storage devices, or another device or devices for storage of data. The data storage 606 may be considered local storage when the data is stored directly on the processor-based device 600 or the data may be accessible to the processor-based device 606 over a wired or a wireless network. The storage device 606 may furthermore include a computer readable storage medium that includes code executable by the processor 602, which may be used, for example, to cause the processor 602 to, at least in part, perform hydrocarbon detection as disclosed herein.

In an embodiment, the storage device 606 for the processor-based device 600 may include a combination of flash storage and RAM. The storage device 606 may also include a computer readable storage medium and may include code executable by the processor 602.

In an embodiment, the elements, including the processor 602, communication adaptor 612, memory 604, input device 610, output device 608, and data storage device 606 may communicate by way of one or more communication busses 614. Those busses 614 may include, for example, a system bus or a peripheral component interface bus.

The processor 602 may be any desired processor and may be a part of a controller 600 or a microcontroller, may be part of or incorporated into another device, or may be a separate device. The processor 602 may, for example, be an Intel® manufactured processor or another processor manufactured by, for example, AMD®, DEC®, or Oracle®. The processor 602 may furthermore execute the program instructions and process the data stored in the memory 604. In one embodiment, the instructions are stored in the memory 604 in a compressed or encrypted format. As used herein the phrase, "executed by a processor," is intended to encompass instructions stored in a compressed or encrypted format, as well as instructions that may be compiled or installed by an installer before being executed by the processor 602.

The data storage device 606 may be, for example, non-volatile battery backed static random-access memory (RAM), a magnetic disk (e.g., hard drive), optical disk (e.g., CD-ROM) or any other device or signal that can store digital information. The data storage device 606 may furthermore have an associated real-time clock, which may be associated with the data storage device 606 directly or through the processor 602. The real-time clock may trigger data from the data storage device 606 to be sent to the processor 602, for example, when the processor 602 polls the data storage device 606. Data from the data storage device 606 that is to be sent across the network 622 through the processor 602 may be sent in the form of messages in packets if desired. Those messages may furthermore be queued in or by the processor 602.

The communication adaptor 612 permits communication between the processor-based device 600 and other nodes, such as a tanker truck controller 35 or a remote monitoring peripheral computer 37, both illustrated in FIGS. 2 and 3, or another computing device or server. The communication adaptor 612 may be a network interface that transfers information from a node such as a networked device, which would include an actuating device such as valve 60 or a sensing device 12,14,16, to the tanker truck controller 35, the remote monitoring peripheral computer 37, a general-purpose computer (not illustrated), a user interface 632, or another node. The communication adaptor 612 may be an Ethernet adaptor or another adaptor for another type of network communication. It will be recognized that the processor-based device 600 may alternatively or in addition be coupled directly to one or more other devices through one or more input/output adaptors (not shown).

The processor-based control device 600 may communicate and may have its memory 604 or processes modified by a user interface 632. That user interface 632 may be, for example, a computer; a tablet; a mobile smartphone device (referred to herein as a phone); an application specific user interface device; or another device that can be used to transfer information to the controller 600 or receive information from the controller 600.

Figure 6:
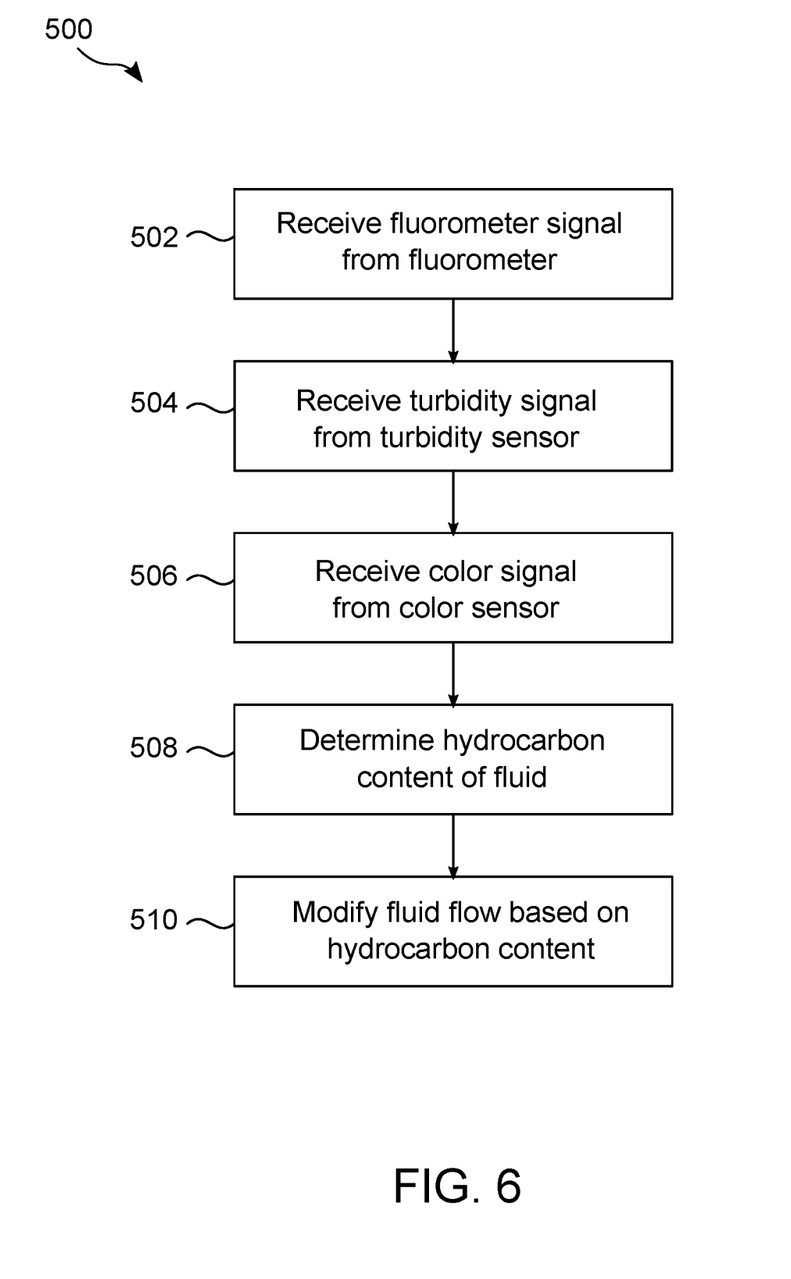
FIG. 6 illustrates an embodiment of a method of detecting hydrocarbon condensate.

FIG. 6 illustrates an embodiment of a method of detecting hydrocarbon condensate in an aqueous mixture 500. At 502, a processor 602, which may be associated with the fluorometer, turbidity sensor, and color sensor or external to those sensors or a controller 600 receives a fluorometer signal from a fluorometer 12, at 504 the processor 602 or controller 600 receives a turbidity signal from a turbidity sensor 14, and at 506 the controller 600 receives a color signal from a color sensor 16. At 508, the processor 602 or controller 600 determines an amount of hydrocarbon content in the aqueous mixture from the fluorescence, the turbidity, and the color of the aqueous mixture. At 510, the processor 602 or controller 600 actuates a control device to modify the flow of the aqueous mixture based on the hydrocarbon content of the aqueous mixture.

The processor 602 or controller 600 may calculate the hydrocarbon content of the aqueous mixture based on the fluorometer signal, the turbidity sensor, and the color sensor. In certain embodiments, the hydrocarbon content may be determined based on the fluorescence of the aqueous mixture with sensed turbidity and color used to correct hydrocarbon content inaccuracies caused by turbidity and color components of the aqueous mixture.

Control of flow of the aqueous mixture may be accomplished in various ways, including closing or switching of a valve 140, 318 and by energizing or de-energizing a pump, compressor, or other component used in the transfer of the aqueous mixture.

A truck tank pressurization system 25 may be provided to provide pressure or vacuum to a truck 210 tank 212. The truck tank pressurization system 25 may be contained within the tanker truck and the truck tank pressurization system 25 may be powered by the tanker truck 210. Alternatively, the truck tank pressurization system 25 may be external to the truck 210, for example at an onloading or offloading site. The truck pressurization system 25 may furthermore be powered externally to the truck, again for example at an onloading or offloading site.

Truck 210 tanks 212 and the vessels they are loading from or unloading into may be pressurized to enhance that process, for example, using the truck tank pressurization system 25. In certain embodiments, when a truck 210 tank 212 is unloading, the tank 212 is pressurized to assist in moving fluid out of the tank 212. In another embodiment, a vessel the tank 212 is unloading into may create a vacuum or negative pressure to assist in drawing the fluid out of the tank 212. In embodiments where the tank 212 is being loaded, a vessel providing fluid to the tank 212 may be pressurized to assist the fluid in moving from the vessel to the tank 212 or the tank 212 may draw a vacuum to assist in moving the fluid from the vessel to the tank 212. In various embodiments, the truck 210 may continue to operate and draw a vacuum until the transfer hose 64 is empty to drain the fluid in the transfer hose 64 into the tank 212. In certain embodiments, the pressure or vacuum may be modified as loading or unloading operations progress, for example, reducing the pressure in a tank 212 as the fluid level in the tank 212 is reduced or reducing the vacuum in the tank 212 as the tank fills. For example, pressure provided to a tank 212 during unloading may be reduced when the tank 212 approaches empty to reduce the amount of air missing with the unloading fluid. As has been mentioned, the operator may shut the production water valve 60 when a tank 212 is filling and full all but the volume of the transfer hose 64, pressure and suction may be removed or de-energized at that time, and once the transfer hose 64 has been emptied into the tank 212, the tank 212 should have a full load of fluid.

The user interface 632 may communicate with the transmitter 600 wirelessly or by a wired connection, for example at the transmitter 600 input/output device coupling 608. The user interface 632 may, for example, be a multi-function communication device, such as an Apple iPhone, a Samsung Galaxy wireless phone, another wireless phone device, a tablet device, or another computing device. The user interface 600 may require input of a password, user facial identification, or other validation to access information contained within the transmitter 600. the user interface may, furthermore, both access data held in the transmitter and configure the transmitter.

The hydrocarbon condensate detection system 10 may include or be housed in an enclosure that is sealed against entry of moisture and solid material and debris and may be surge protected to protect against electrical overload. Communications between the hydrocarbon condensate detection system 10 may furthermore be password protected with unique passwords. Those passwords may relate to a customer, organization, site, or otherwise as desired to restrict access to information to those having a legitimate interest in the information to be shared between devices.

The hydrocarbon condensate detection system 10 may also include one or more indicators 634 that extend through its enclosure to provide operational information to an onlooker. For example, the indicators 634 may include one or more LEDs that indicate information such as operating status of the transmitter 600 and communication between the transmitter 600 and another node. The indicators 634 may furthermore include one or more readouts that indicate, for example, the signal being received by the transmitter 600 or the signal being or to be transmitted by the transmitter 600.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A hydrocarbon detection and control system for an aqueous mixture, comprising:
   a controller having a plurality of inputs and at least one output;
   a fluorometer coupled to a first input of the controller, the fluorometer sensing hydrocarbon fluorescence in an aqueous mixture and providing a signal to the controller commensurate with an amount of hydrocarbons in the aqueous mixture;
   a color sensor sensing color of the aqueous mixture coupled to a second input of the controller, the color sensor providing a signal commensurate with aqueous mixture color to the second input of the controller;
   a turbidity sensor coupled to a third input of the controller, the turbidity sensor sensing turbidity in the aqueous mixture and providing a signal to the third input of the controller commensurate with turbidity of the aqueous mixture; and
   a control device coupled to the controller output, the control device modifying flow of the aqueous mixture.

2. The hydrocarbon detection and control system of claim 1, wherein the hydrocarbon detection and control system is attached to an outlet of a tanker truck tank to sense hydrocarbon content of aqueous mixture leaving the tank.

3. The hydrocarbon detection and control system of claim 2, further comprising identifying a truck unloading the aqueous mixture to the controller.

4. The hydrocarbon detection and control system of claim 1, wherein the hydrocarbon detection and control system is attached to a tank to sense hydrocarbon content of aqueous mixture leaving the tank.

5. The hydrocarbon detection and control system of claim 4, wherein the controller stops the transfer of the aqueous mixture.

6. The hydrocarbon detection and control system of claim 5, wherein the aqueous mixture transfer is stopped by one of closing a valve, de-energizing a pump, de-energizing a compressor, and by notifying an operator of the high hydrocarbon content of the aqueous mixture.

7. The hydrocarbon detection and control system of claim 4, wherein the controller redirects the transfer of the aqueous mixture from an aqueous mixture reservoir to a hydrocarbon and aqueous mixture reservoir.

8. The hydrocarbon detection and control system of claim 7, wherein the controller redirects the transfer of the aqueous mixture from an aqueous mixture reservoir to a hydrocarbon and aqueous mixture reservoir by one of a valve and by notifying an operator of the high hydrocarbon content of the aqueous mixture.

9. The hydrocarbon detection and control system of claim 1, wherein modifying flow of the aqueous mixture includes modifying flow on one of a plurality of aqueous mixture pipelines feeding a common pipeline.

10. A multi-input pipeline hydrocarbon detection and control system, comprising:
   a plurality of pipelines, each to receive aqueous process fluid from a single separate unloading station and discharge that aqueous process fluid into a common manifold pipeline, each unloading station having a processor containing instructions which, when executed by the processor cause the processor to;
   receive a fluorescence signal from a fluorometer at a first input, the fluorometer to sense hydrocarbon fluorescence in an aqueous process fluid and the fluorescence signal indicating an amount of hydrocarbon content in the aqueous process fluid;
   receive a color signal from a color sensor at a second input, the color sensor to sense the color of the aqueous process fluid and the color signal indicating the color of the aqueous process fluid;
   receive a turbidity signal from a turbidity sensor at a third input, the turbidity sensor to sense turbidity of the aqueous process fluid and the turbidity signal indicating the turbidity of the aqueous process fluid; and
   transmit a control signal to a control device coupled to an output, the control device to modifying flow of the aqueous process fluid.

11. The multi-input pipeline hydrocarbon detection and control system of claim 10, wherein the common manifold pipeline discharges the aqueous process fluid into a storage vessel, further comprising a flow meter situated in the common manifold pipeline that provides a total manifold system flow to the processor at a fourth input.

12. The multi-input pipeline hydrocarbon detection and control system of claim 10, wherein the control device to modify flow of the aqueous process fluid controls flow through a single offloading station.

13. The multi-input pipeline hydrocarbon detection and control system of claim 12, wherein the control device to modify flow of the aqueous process fluid through a single offloading station is a valve.

14. The multi-input pipeline hydrocarbon detection and control system of claim 12, further comprising identifying a truck unloading the aqueous mixture to the controller.

15. A method of detecting hydrocarbon in an aqueous mixture and controlling flow of that aqueous mixture, comprising:
   receiving a fluorescence signal from a fluorometer sensing hydrocarbon fluorescence in an aqueous mixture;
   receiving a color signal from a color sensor sensing the color of the aqueous mixture;
   receiving a turbidity signal from a turbidity sensor sensing turbidity of the aqueous mixture;
   calculating hydrocarbon content of the aqueous mixture from the sensed fluorescence, color and turbidity of the aqueous mixture; and
   controlling the flow of the aqueous mixture based on the hydrocarbon content of the aqueous mixture.

16. The method of claim 15, wherein the flow of the aqueous mixture is stopped when hydrocarbon content of the aqueous mixture exceeds a predetermined limit.

17. The method of claim 16, wherein flow of the aqueous mixture is stopped through only one of a plurality of unloading stations flowing into a common pipeline.

18. The method of claim 17 further comprising identifying a truck unloading the aqueous mixture the flow of which is stopped.

19. The method of claim 15, further comprising notifying an operator of when high hydrocarbon content is sensed in the aqueous mixture.

20. The method of claim 19, further comprising redirecting the transfer of the aqueous mixture from an aqueous mixture reservoir to a hydrocarbon and aqueous mixture reservoir when high hydrocarbon content is sensed in the aqueous mixture.

* * * * *